United States Patent
Heikkilä et al.

[11] Patent Number: 6,104,947
[45] Date of Patent: Aug. 15, 2000

[54] METHOD AND APPARATUS FOR DETERMINING EXERTION LEVELS IN FITNESS OR ATHLETIC TRAINING AND FOR DETERMINING THE STRESS CAUSED BY TRAINING

[75] Inventors: Ilkka Heikkilä; Arto Pietilä, both of Oulu, Finland

[73] Assignee: Polar Electro Oy, Kempele, Finland

[21] Appl. No.: 08/702,516

[22] PCT Filed: Dec. 28, 1995

[86] PCT No.: PCT/FI95/00713

§ 371 Date: Oct. 15, 1996

§ 102(e) Date: Oct. 15, 1996

[87] PCT Pub. No.: WO96/20640

PCT Pub. Date: Jul. 11, 1996

[30] Foreign Application Priority Data

Dec. 29, 1994 [FI] Finland .................................. 946164

[51] Int. Cl.[7] .................................................. A61B 5/0456
[52] U.S. Cl. ............................................. 600/519; 600/521
[58] Field of Search ........................... 600/519, 521, 600/515–518, 520; 482/8, 9, 900–902

[56] References Cited

U.S. PATENT DOCUMENTS

| | | |
|---|---|---|
| 3,978,849 | 9/1976 | Geneen . |
| 4,202,350 | 5/1980 | Walton . |
| 4,367,752 | 1/1983 | Jimenez et al. . |
| 4,566,461 | 1/1986 | Lubell et al. . |
| 4,625,733 | 12/1986 | Säynäjäkangas . |
| 4,732,157 | 3/1988 | Kaplan et al. ..................... 128/696 |
| 5,048,535 | 9/1991 | Maruyama . |
| 5,265,617 | 11/1993 | Verrier et al. . |
| 5,277,189 | 1/1994 | Jacobs .............................. 128/696 |
| 5,277,190 | 1/1994 | Moulton ........................... 128/705 |
| 5,291,400 | 3/1994 | Gilham ............................. 128/702 |
| 5,297,558 | 3/1994 | Acorn et al. . |
| 5,299,119 | 3/1994 | Kraf et al. . |
| 5,314,389 | 5/1994 | Dotan . |
| 5,323,784 | 6/1994 | Shu . |
| 5,339,822 | 8/1994 | Taylor et al. . |
| 5,419,338 | 5/1995 | Sarma et al. ..................... 128/703 |
| 5,423,325 | 6/1995 | Burton ............................. 128/702 |

FOREIGN PATENT DOCUMENTS

| | | |
|---|---|---|
| 0 225 621 A1 | 2/1988 | European Pat. Off. . |
| 0 379 227 A3 | 7/1990 | European Pat. Off. . |
| 0 485 981 A3 | 5/1992 | European Pat. Off. . |
| 0 553 372 A1 | 8/1993 | European Pat. Off. . |
| 3439 238 A1 | 5/1985 | Germany . |
| 6105819 | 4/1994 | Japan ............................... 128/708 |
| WO 90/09144 | 8/1990 | WIPO . |
| WO 91/01685 | 2/1991 | WIPO . |

*Primary Examiner*—Jeffrey R. Jastrzab
*Attorney, Agent, or Firm*—Hoffmann & Baron, LLP

[57] ABSTRACT

The present invention relates to a method and an apparatus for determining exertion levels in fitness or athletic training and for determining the stress caused by training. According to the invention, the ECG signal of a person and the timing moment of at least one waveform of the ECG signal, for instance the QRS complex, are measured by means of a heartbeat rate monitor during a training period. The heartbeat rate is calculated on the basis of corresponding ECG signal waveform distances, and a value proportional to the magnitude of the heartbeat rate variation or to that of a total or partial power of a spectrum derived from the heartbeat rate is provided by means of a mathematical function. Those exertion levels of the person which are essential as regards to training period or the stress caused by the training in relation to the exertion levels are determined on the basis of the heartbeat rate variation.

21 Claims, 9 Drawing Sheets

FIG. 1

FIG. 2  HEARTBEAT RATE VARIATION DURING EXERTION

FIG. 7b $RR_1 = t_2 - t_1,\quad RR_2 = t_3 - t_2,\ \ldots$

METHOD AND APPARATUS FOR DETERMINING EXERTION LEVELS IN FITNESS OR ATHLETIC TRAINING AND FOR DETERMINING THE STRESS CAUSED BY TRAINING

BACKGROUND OF THE INVENTION

1. Field of the Invention

The present invention relates to a method and an apparatus for determining exertion levels in fitness or athletic training and for determining the stress caused by training by means of heartbeat rate measurement.

2. Description of the Prior Art

Heartbeat rate measurement is used in fitness and athletic training for determining working capacity or a stress level. This is based on the observation that an almost linear dependency exists between heartbeat rate and increasing working capacity within the main exertion area. The change in the energy production processes of vital functions, such as respiration, heartbeat rate and muscular action, i.e. metabolism, is generally used in determining exertion levels, for instance by means of lactic acid, which is a waste material of the energy production processes.

When a person starts the training, the lactic acid content of muscles and blood falls at first slightly below the starting level. This is due to stimulated circulation, and to lactic acid decomposition and removal processes improving with muscular action. Thereafter, when the exertion level is steadily increased, the lactic acid content starts to increase linearly in relation to the stress. The working capacity at which the lactic acid content reaches its starting value is referred to as the aerobic threshold, at which corresponding vital function levels, such as heartbeat rate frequency and oxygen consumption, can be determined.

At working capacities lower than the aerobic threshold, energy is produced aerobically, i.e. by burning mainly fats and a small amount of carbohydrates by means of oxygen. At working capacities higher than the threshold, energy is produced to an ever-increasing degree anaerobically, i.e. in a manner involving an oxygen debt, whereby more and more lactic acid is correspondingly produced in the tissues. At the same time, the proportional amount of the use of fats in energy production decreases, and carbohydrates become the main source of energy.

When the performance level is further increased, a situation finally arrives where the system is no longer capable of processing the amount of lactic acid produced in energy production. The disturbance of the balance is detected as an abruptly increasing content of lactic acid in the blood and as a distinct increase in lung ventilation, taking place at the same time. This exertion level, which is significant as regards training, is referred to as the anaerobic threshold.

The exact determination of the aerobic and anaerobic threshold is carried out today in special test laboratories by means of a maximum stress test based on breathing gas analysis. The test is started with a small stress. The stress is increased without an intermission by small steps at intervals of 2–3 minutes all the way to the maximum exertion. From the last 30 seconds of each stress level, the ventilation, used oxygen, and produced carbondioxide are registered, and a blood sample is taken to determine the lactic acid level. The threshold values are determined by means of the lactic acid and the breathing parameters. However, the results are clearly affected by the manner of applying the stress, the speed of increasing the stress, and the stress levels used, whereby threshold values of different magnitudes are obtained in different physical stress situations, for instance with the use of a running mat and an ergometer. On the other hand, the repeatability of the aerobic and anaerobic thresholds is questionable; for instance in increasing the stress in a sliding manner and not by steps, the threshold phenomena can not be detected. Reference is made for instance to U.S. Pat. No. 5,297,558, according to which a person must be subjected, in determining the exertion level of the person, to exertion increasing by steps during the training period in order that the points of discontinuity in the heartbeat rate variation graph, indicating the limits of different exertion levels, would appear sufficiently clearly.

Today, the determinations of the aerobic and anaerobic thresholds are primarily used in training endurance athletes to determine suitable training capacities and to monitor the effects of the training. Similarly, the thresholds can be used for determining optimum training capacities e.g. for a dieting person. When heartbeat rate values corresponding to the thresholds are known, a desired training capacity can be accurately maintained by means of continuous heartbeat rate monitoring. The presently available methods for determining the threshold values are based on difficult lactic acid or breathing gas measurements, in which the taking of blood samples, expensive laboratory equipment and staff requirements play a significant part. Furthermore, the determinations are based on a phenomenon the repeatability of which has not been possible to verify.

The aerobic and anaerobic thresholds are thus mainly used in monitoring the performance level of athletes. As regards a person engaged in fitness training, the situation is entirely different. Few people have the possibility to have expensive laboratory measurements to determine the threshold values. On the other hand, the needs of a person engaged in fitness training differ from those of athletes. The correct exertion level of a person engaged in fitness training is represented by exercise which is sufficient for maintaining health and improving fitness but which does not exceed the limit of safe exertion. The need for anaerobic training is small, and aerobic training is emphasized. For the needs of persons engaged in fitness training, a heartbeat rate range can be divided into four target heartbeat rate ranges. The lowest capacity range, within which the heartbeat rate is not more than 55% of the maximum heartbeat rate, does not yet provide a sufficient training response. In moving within a capacity range of 55–65% of the maximum heartbeat rate, an efficient use of fats starts. The actual target heartbeat rate range in aerobic training, 65–85% of the maximum heartbeat rate, provides the best final result in target-oriented fitness training. With a heartbeat rate higher than this, energy production rises partly to a distinctly anaerobic area. In the presently widely used method for determining the target heartbeat rate ranges, the correct exertion levels are determined as based on the measured or estimated maximum heartbeat rate of a person engaged in fitness training. The maximum heartbeat rate can be accurately measured during extreme exertion, but this may cause a health risk especially as regards beginners in fitness training. Generally, the maximum heartbeat rate and training heartbeat rates are estimated on the basis of the age of the person engaged in fitness training from a calculation formula, or by means of the resting heartbeat rate and the maximum heartbeat rate by the so-called Karvonen method. Since maximum and resting heartbeat rates are individual, the error margin of the estimation methods is great. On the other hand, the threshold values are not fixed but they vary for instance when the level of fitness changes. For instance, the anaerobic threshold corresponds to about 60–75% of the maximum heartbeat rate with persons who have not trained and who are in poor condition. For an athlete who has trained for a long time and who is in top condition, the threshold may be even more than 80% of the maximum heartbeat rate. Due to this, the definition of target heartbeat rate ranges fails for a majority of persons engaged in fitness training, and the advantages of the method remain scarce.

When contracting, a heart produces a series of electric pulses, which can be measured everywhere in a body. The measurement and analysis of such a signal is referred to as electrocardiography (ECG). The actual signal is referred to as an ECG signal. In an ECG signal, it is possible to distinguish phases resulting from different operational stages of the heart. These portions are the so-called P, Q, R, S, T and U-waves (cf. FIG. 1), which will be described in more detail below.

Due to the variation in the sympathetic-parasympathetic balance of the autonomic nervous system, variations around the average heartbeat rate level occur constantly in heartbeat rate. The variation in heartbeat rate is caused by the function of the cardiovascular control system. The main reasons for the variation are respiratory arrhythmia, variation caused by blood pressure control, and variation caused by the heat balance control of the system. Among these, the most significant and causing the greatest variation is respiratory arrhythmia. The transmitting nervous systems of heartbeat rate variation can be distinguished by means of heartbeat rate variation frequency analysis. At the present time, the sympathetic nervous system is considered to be slow; it is hardly capable of transmitting frequencies higher than 0.15 Hz. Instead, the operation of the parasympathetic nervous system is fast, wherefore frequencies higher than the above-mentioned threshold frequency are transmitted through the parasympathetic nervous system.

Heartbeat rate variation can be measured for instance by means of standard deviation. Other generally used variation measuring units are spectrum calculation power values, the maximum value of the variation, and the height of the deviation diagram. The standard deviation does not distinguish the frequency components of intervals between R-wave peaks, i.e. R—R intervals, but it is affected by frequencies transmitted from both autonomic nervous systems. In measuring the standard deviation of short-term R—R-intervals during exertion, it can be stated, justifiably and in a partly simplified manner, that the standard deviation measures almost exclusively the proportion of parasympathetic control in the heartbeat rate variation. This is mainly due to the fact that the greatest source of variation (respiratory frequency) during exertion rises unavoidably higher than those frequencies which the sympathetic nervous system is capable of transmitting.

In increasing the exertion level from the resting level, the parasympathetic tonus decreases at first by degrees. When the heartbeat rate level has risen to a level of about 100 pulsations/min, i.e. to about 56% of the maximum heartbeat rate, the sympathetic activity starts to rise, and will have a significant effect on the heartbeat rate frequency at a level of about 63% of the maximum heartbeat rate. With low exertion, an increase in the heartbeat rate is almost completely due to decreased parasympathetic activity. The heartbeat rate variation thus decreases in a direct proportion to the disappearance of the parasympathetic control. It is only on a higher exertion level that the sympathetic nervous system participates in controlling the heartbeat rate level with the parasympathetic one.

Respiratory arrhythmia has been found to be the most important cause of heartbeat rate variation. The strength of respiratory arrhythmia depends both on the deepness of respiration and respiratory frequency. The maximum amplitude is reached at a respiratory frequency of 5–7 times per minute. Furthermore, respiratory arrhythmia attenuates strongly as the respiratory frequency increases. The deepness of the respiration affects the strength of arrhythmia up to a level corresponding to 50–60% of the respiratory capacity. At a volume higher than this, the respiratory arrhythmia no longer increases. During fitness training, the respiratory volume always exceeds this limit point, wherefore the effect thereof can be ignored in this context. The heartbeat rate variation during a performance can thus be regarded as representing the respiratory frequency of the person engaged in fitness training to a large extent. Furthermore, empirical knowledge concerning fitness training is that if a person engaged in fitness training is able to carry on a conversation during his performance, the exertion level is suitable and the fitness training is aerobic. The energy requirement of the system can thus be satisfied without anaerobic energy production, and lactic acid causing subsequent soreness of muscles does not accumulate in the system. On the other hand, if the person engaged in fitness training is able to speak, his entire respiratory capacity is not used. Relaxed respiration causes relatively wide heartbeat rate variation. If the exertion level of the person engaged in fitness training approaches the anaerobic area, he must unavoidably start using his entire respiratory capacity. The respiration is smooth and quick-paced, heartbeat rate variation thus remaining low.

OBJECTS AND SUMMARY OF THE INVENTION

The object of the present invention is to provide new types of methods and apparatuses for determining and controlling individual training capacities of persons engaged in fitness and athletic training. As implemented according to the principles of the invention, determination of a personal exertion level in each situation is easy and possible to be carried out by anyone. The method does not necessarily require equipment other than a heartbeat rate monitor equipped with the functions according to the invention.

By using, according to the invention, heartbeat rate variation in determining training capacity, it is possible to implement individual target heartbeat rate range determination which is sufficiently accurate for the needs of a person engaged in fitness training, and which adapts to changes occurring in the system of the person engaged in the training. The invention thus enables real-time and wireless monitoring of heartbeat rate variation and thus the optimization of the training of the person engaged in fitness training without threshold value determination measurements carried out in laboratories.

The methods and the apparatuses of the invention are characterized by what is disclosed in the claims below.

BRIEF DESCRIPTION OF THE DRAWINGS

In the following, the invention will be described in more detail by means of examples with reference to the accompanying drawings, in which.

DETAILED DESCRIPTION OF THE PREFERRED EMBODIMENTS

Figure 1:
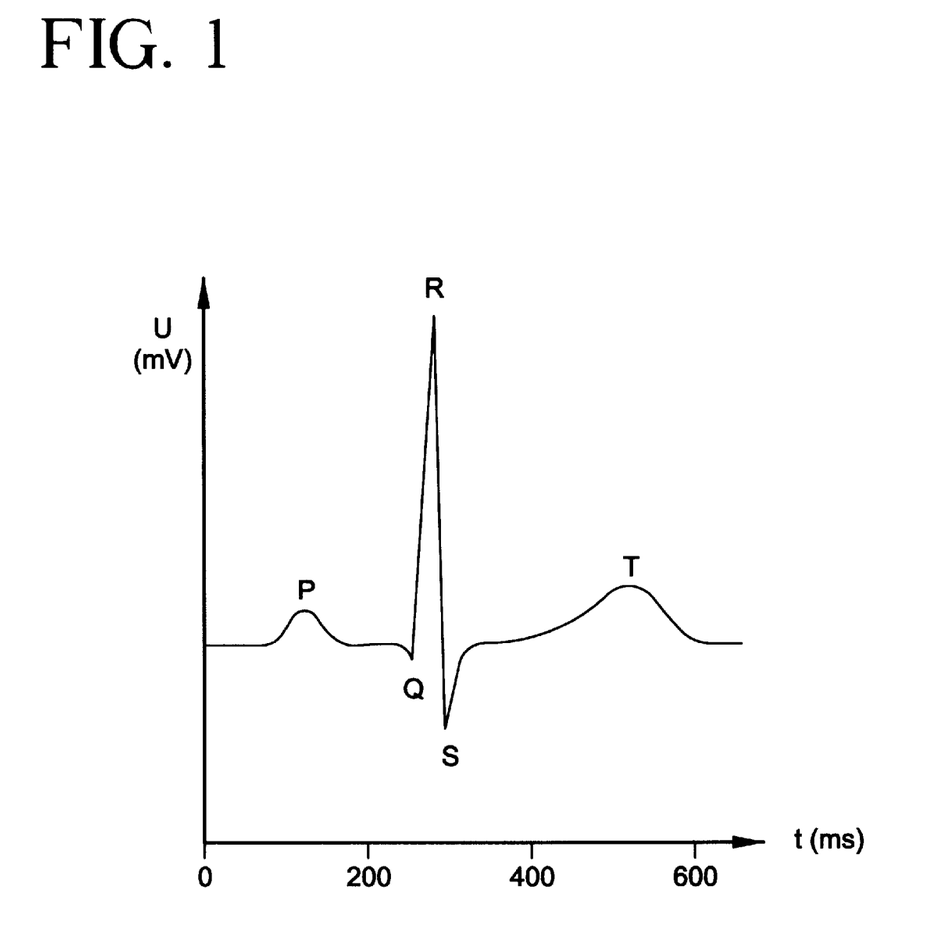
FIG. 1 shows the shape of an ECG signal caused by heartbeat rate.

FIG. 1 shows a typical ECG signal caused by heartbeat rate as presented in a time-voltage coordinate system. The above-mentioned P, Q, R, S, and T-waves can be distinguished in each signal by an accurate measurement, cf. for instance U.S. Pat. No. 5,299,119. The highest value R represents the maximum point of an ECG signal, and the pulsation defined by the points Q, R and S, i.e. the QRS complex, represents the most easily distinguishable part of the ECG signal. The interval between two successive R peak values is often referred to as the R—R interval of the ECG signal. A P-wave is caused by the contraction of the atria. When the atria contract, the ventricles are filled with blood. The QRS complex formed by the peaks of three waves, defining the shape of the R peak of the ECG signal, is produced when the ventricles contract. The right ventricle thus pumps blood from veins to the lungs, and the left ventricle pumps blood from the lungs to arteries. The repolarization of the ventricle muscles causes a T-wave, which is lower and more even than the R peak. The periods between the waves depend on the speed of propagation of the nervous stimulus in the heart. The operation of the pacemaker of the heart, i.e. the sinoatrial node, is not visible in an ECG signal.

In a healthy human, the ECG signal is between 1 and 2 mV in amplitude as measured on the skin. For instance, the amplitude value and duration given for an R peak in literature are 1.6 mV and 90 ms, whereas the corresponding values for a P-wave are 0.25 mV and 110 ms. When the heartbeat rate accelerates as a result of exertion, the durations and amplitudes of the different components of the ECG signal remain almost unchanged. It is thus known that the accurate measurement of heartbeat rate and related phenomena is possible by analyzing the ECG signal of heartbeat rate.

The easiest starting point for determining the timing point of an ECG signal accurately is the detection of the QRS complex. In a disturbance-free situation, the QRS complex can be detected in a fairly simple manner by means of a peak value detector. To reduce the number of disturbances occurring in practical situations, some type of filtering is used in accurate analyses. The following examples can be mentioned:

band pass filtering, by which the frequencies included in the QRS complex are emphasized, and in which the QRS complexes are separated from a filtered signal by using some non-linear inference rule, which is based on some easily distinguishable characteristic of the QRS complex, such as the speed of rising, amplitude, etc.

matched filtering, in which the QRS complex is modelled for instance in a FIR filter by the filter coefficients, and a cross correlation is calculated between the incoming signal and the QRS complex provided as coefficients.

pattern recognition method, in which the processed signal is parametrisized into a series of peaks of different widths and heights. By means of pattern recognition, the peaks due to the operational stages of the heart are recognized, if possible, in an ECG signal. The method can also be used for detecting timing points other than those based on the QRS complex.

The development of microprocessors enables the implementation of more and more complicated digital filter structures without the size of the apparatus and current consumption increasing. The timing point recognition methods listed briefly above thus constitute only a part of viable algorithms, and more methods are continuously being developed.

Figure 2:
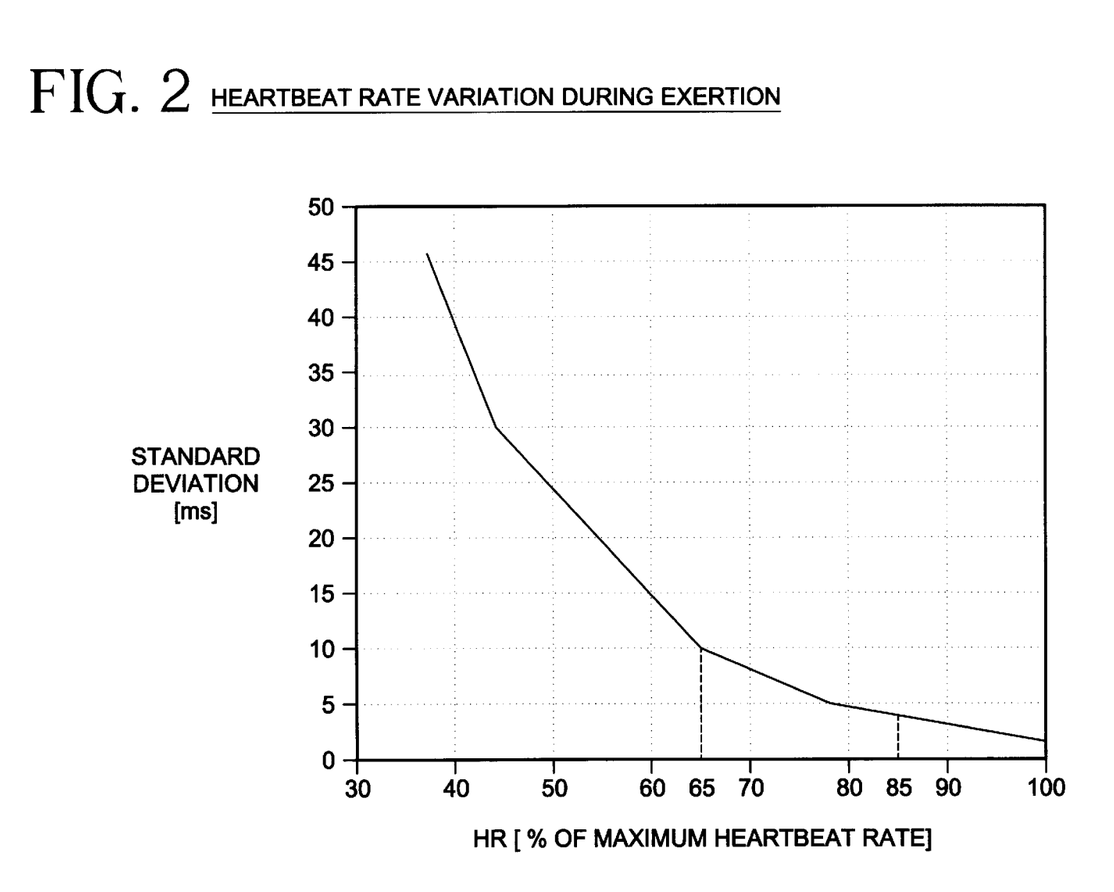
FIG. 2 shows a heartbeat rate variation graph during stress.

FIG. 2 shows the behaviour of heartbeat rate variation according to the level of exertion. The graph is drawn on the basis of standard deviations calculated from 100 successive R—R intervals. The figure shows a distinct non-linear decrease in the variation when the exertion is increased. If the generally accepted upper and lower limits of the aerobic training range, 85% and 65% of the maximum heartbeat rate level, are drawn in the figure, it can be observed that they coincide with the points 4 ms and 10 ms on the variation axis, respectively. It has been noticed in studies that the level of heartbeat rate variation distinctly correlates with other physiological quantities measured during exertion, such as maximum oxygen uptake capacity, ventilation threshold, or anaerobic threshold. The graph according to FIG. 2 is user, sport, and measurement period specific. The variation graph is thus shown here only by way of example since if some of the mentioned starting points change, the limiting points of the graph may deviate from what is shown here.

In existing heartbeat rate monitors which filter heartbeat rate, the averaging which levels instantaneous heartbeat rate variation prevents the heartbeat rate variation from being analyzed in more detail. In signal processing, averaging means low pass filtering, which as used in this connection cuts the fast variation signal away from the heartbeat rate signal.

In the method of the invention, an ECG signal is measured at the chest or some other body part of a person engaged in fitness training, and this signal is transmitted to a receiver as in existing heartbeat rate monitors. The resolution of the heartbeat rate transmitter in defining the timing information of successive ECG signals is at least in the range of 1 ms. The heartbeat rate of the exercising person is constantly monitored during the entire performance. The heartbeat rate monitor measures, as deviating from averaging monitors, some unambiguous timing point of each ECG signal, for instance the R—R interval obtained from QRS complexes, and calculates the standard deviation of the heartbeat rate or some other variation index from the collected intervals. The heartbeat rate monitor constantly monitors the development of the variation and gives a corresponding target heartbeat rate range, or alternatively gives an alarm if a previously set target heartbeat rate range is exceeded or fallen short of.

Figure 3:
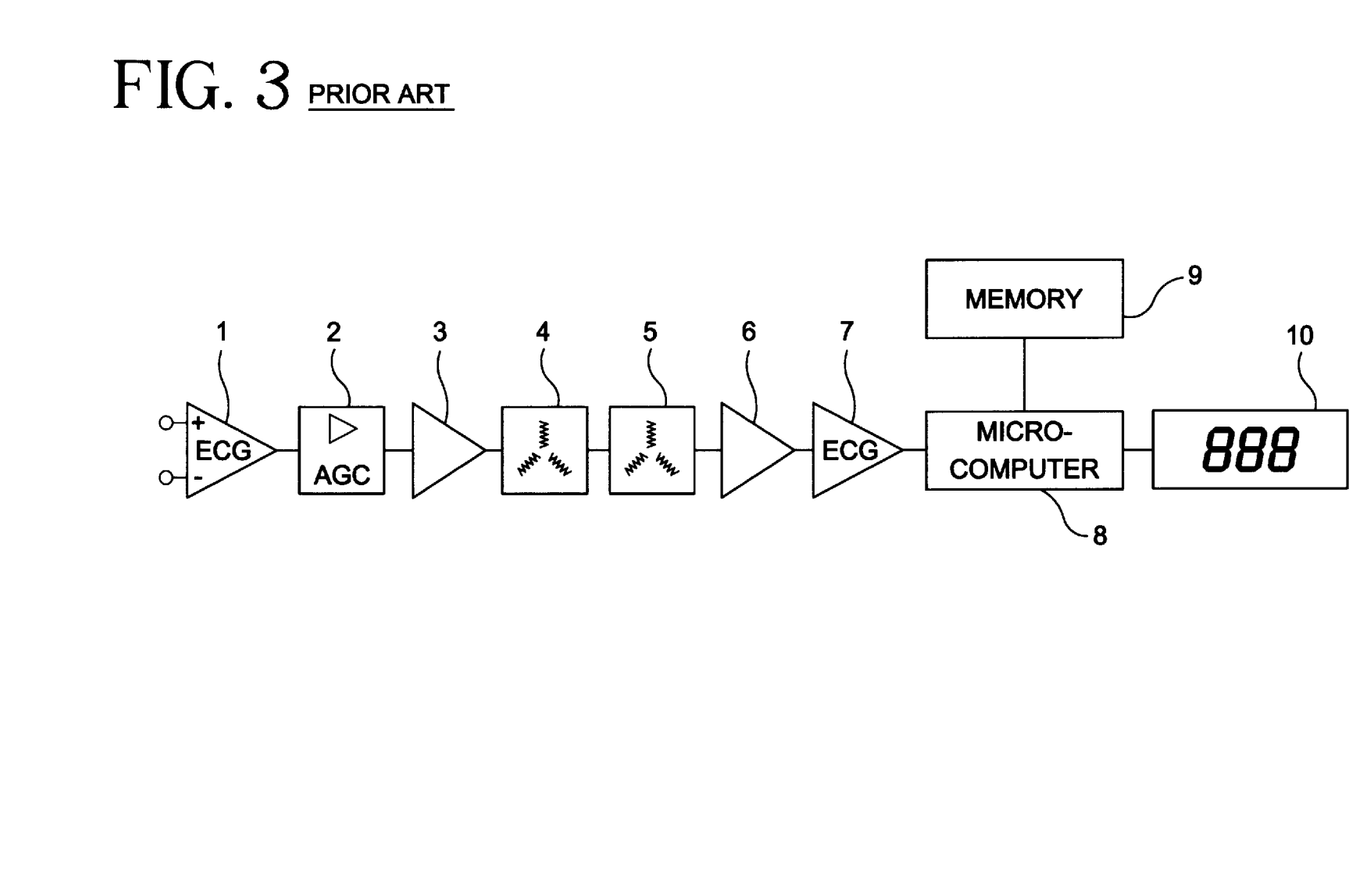
FIG. 3 shows a general view of the apparatus of the invention.

FIG. 3 shows a schematic view of the exemplifying apparatus of the invention. As examined on this level, the apparatus does not differ from conventional wireless heartbeat rate monitors, as an example of which the heartbeat rate monitor disclosed in U.S. Pat. No. 4,625,733 can be mentioned (FIG. 3). In the telemetric heartbeat rate monitor shown in FIG. 3, ECG electrodes (not shown) are connected to the differential input poles of an ECG pre-amplifier 1. The heartbeat rate signal provided by the pre-amplifier is amplified in an AGC amplifier 2, which is used for controlling a power amplifier 3, in which is produced a heartbeat rate signal controlling coils 4, the interval between the pulses of the signal being the same as the interval between the heart pulsations. A magnetic field varying with the rhythm of the heartbeat rate is thus generated in the coils 4. The magnetic field detected by receiving coils 5 is amplified in a sensitive pre-amplifier 6, whereafter the signal is applied to a signal amplifier 7. The output signal of the amplifier is processed in a microcomputer 8, which stores the heartbeat rate information it has calculated in a memory 9, calculates heartbeat rate variation information etc., and indicates the requested data on a liquid crystal display 10.

Figure 4:
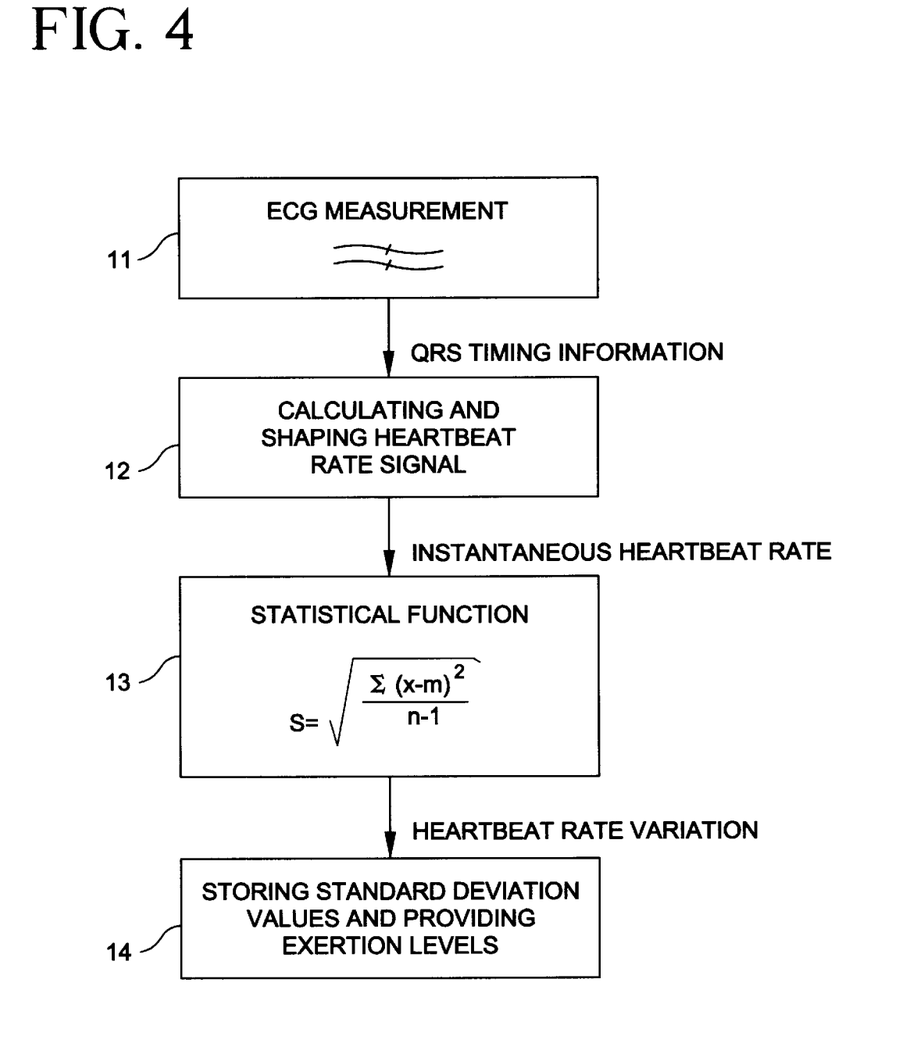
FIG. 4 shows a functional diagram of the apparatus according to an embodiment of the invention.

FIG. 4 shows a functional diagram of the apparatus according to an embodiment of the invention. The functions according to the diagram are preferably included in the software of the computer 8 of the heartbeat rate monitor. The purpose is to determine the exertion levels of a person engaged in fitness or athletic training by measuring his heartbeat rate and analyzing the measurement results. Depending on whether the desired training period is partly aerobic, i.e. basic endurance training, pace endurance training, anaerobic interval training or other training monitored by means of heartbeat rate variation, it is possible to determine (cf. FIG. 2), by means of the invention, those exertion levels, i.e. heartbeat rate variation ranges, within which a desired energy metabolism process of the body exists. Training taking place in the aerobic area and one taking place in the anaerobic area represent, precisely, different energy metabolism processes.

In FIG. 4, the heartbeat rate measurement which is the basis of the operation is carried out in block 11. By means of the heartbeat rate monitor, the heartbeat rate of a person and the timing moment of at least one waveform of the ECG signal, for instance the QRS complex, are measured during the training period.

Thereafter, the instantaneous heartbeat rate is calculated in block 12 on the basis of corresponding ECG signal waveform distances, and a possible shaping is carried out for instance with a suitable digital filter. The heartbeat rate signal can be preferably high pass filtered in this connection to remove slow processes distorting the result, these processes being due for instance to sudden changes in load levels.

A value proportional to the magnitude of the heartbeat rate variation or to that of the total or partial power of a spectrum derived from the heartbeat rate is provided by means of a statistical function 13, i.e. by the formula of the standard deviation s in this example. The heartbeat rate variation can also be calculated for instance by means of the height or width of the heartbeat rate variation distribution pattern or by means of a statistical function provided by a quantity derived from the height and width.

The heartbeat rate variation values calculated during the training period are registered, i.e. stored, in block 14 as a time function. At the same time is produced a graph derived from the heartbeat rate variation values (cf. FIG. 2), which indicates at least those exertion levels of the person which are essential as regards the training period concerned.

Figure 5:
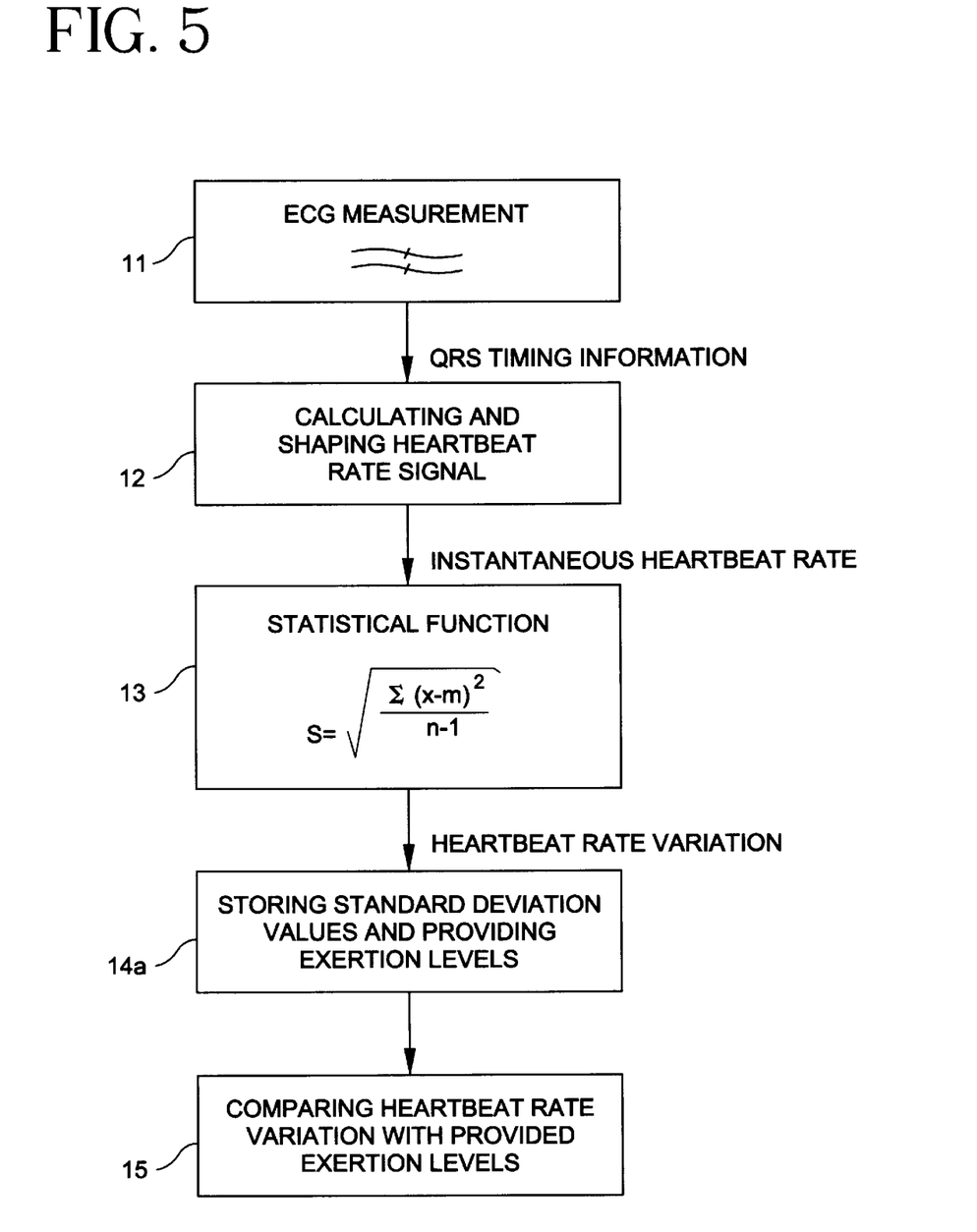
FIG. 5 shows a functional diagram of the apparatus according to a second embodiment of the invention.

FIG. 5 shows a functional diagram of the apparatus according to a second embodiment of the invention. In this case also, the functions according to the diagram are preferably included in the software of the computer 8 of the heartbeat rate monitor. The purpose here is to determine not only the exertion levels of a person engaged in fitness or athletic training but also the stress caused by the training he performs.

As in FIG. 4, the heartbeat rate of a person and the timing moment of at least one waveform of the ECG signal are measured during the training period by means of a heartbeat rate monitor in block 11. The instantaneous heartbeat rate is calculated in block 12 on the basis of corresponding ECG signal waveform distances, and a possible shaping is carried out for instance with a suitable digital filter. In this example also, a statistical function, such as standard deviation s, is used in block 13 for providing a value proportional to the magnitude of the heartbeat rate variation or to that of the total or partial power of a spectrum derived from the instantaneous heartbeat rate. The values proportional to the heartbeat rate variation are registered and stored at least at the beginning of the training period, within a determined time period, in block 14a as a time function for determining at least those exertion levels of the person which are essential as regards the training period concerned. Finally, as the training continues past this time period, the instantaneous heartbeat rate variation of the person is compared in block 15 with the corresponding heartbeat rate variation values of the determined exertion levels, and the stress caused by the training in relation to the exertion levels, calculated on the basis of the instantaneous heartbeat rate variation, is indicated on the heartbeat rate monitor.

Thus, the heartbeat rate monitor of the invention is capable of determining fully automatically, at the beginning of a training period, the target heartbeat rate ranges of a user by means of heartbeat rate variation, without the user having to program this separately.

The apparatus of the invention, which preferably consists of a heartbeat rate monitor, comprises a memory, in which it is possible to program in advance different exertion levels of a person, such as heartbeat rate variation ranges corresponding to the threshold values of energy metabolism. By means of heartbeat rate variation threshold value settings, it is thus possible to program in advance training of a desired type, which may be partly aerobic, i.e. basic endurance training, pace endurance training, anaerobic interval training or other training monitored by means of heartbeat rate variation. In practise, a training person is notified, when he is performing a training period the stress of which preferably increases gradually, for instance by means of a sound signal when the target heartbeat rare variation range is reached.

Figure 6:
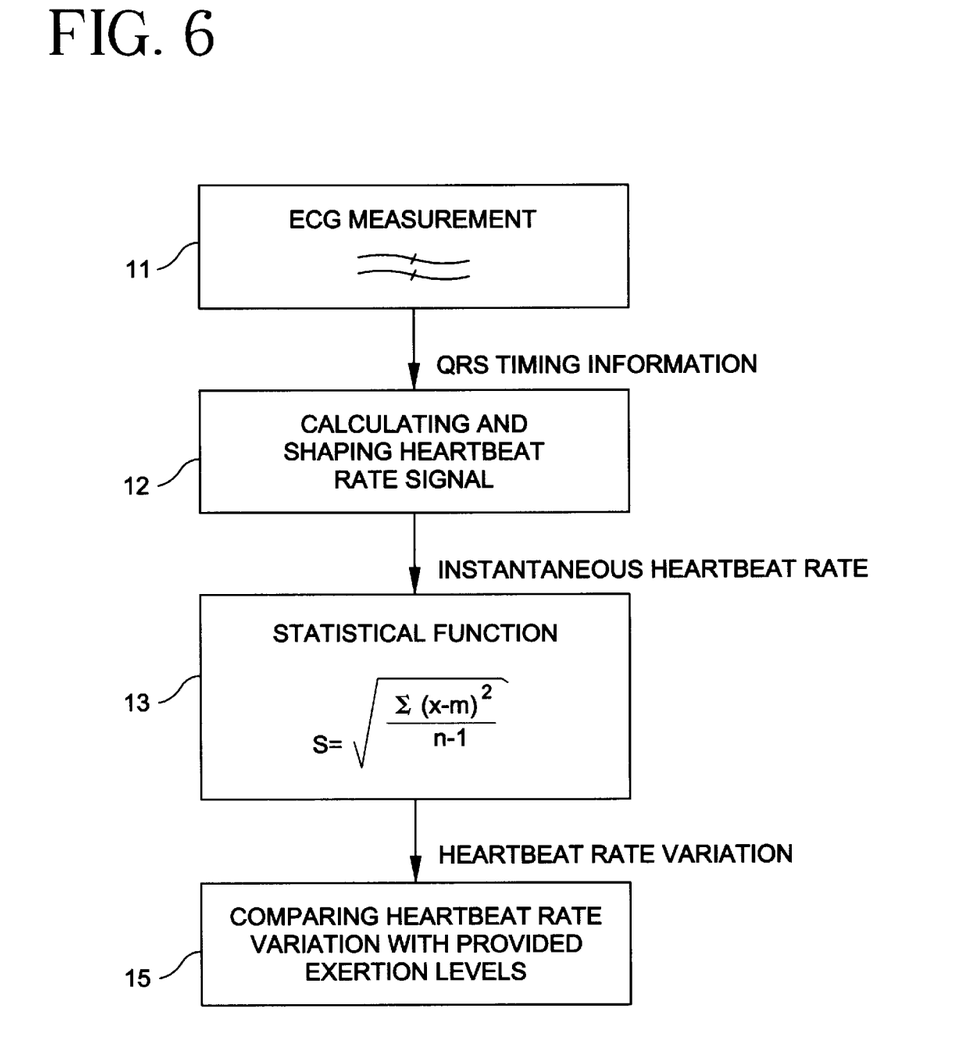
FIG. 6 shows a functional diagram of the apparatus according to a third embodiment of the invention.

FIG. 6 shows a functional diagram of the apparatus according to a third embodiment of the invention. In this case, the object is merely to control the stress caused by training performed by a person engaged in fitness or athletic training by means of heartbeat rate measurement. As described in connection with FIGS. 4 and 5, the heartbeat rate measurement which is the basis of the operation is carried out in block 11. By means of the heartbeat rate monitor, the heartbeat rate of a person and at least one fixed point of the ECG signal (the QRS complex) are measured during the training period. The heartbeat rate is calculated in block 12 on the basis of the ECG signals, and a possible shaping is carried out for instance with a suitable digital filter. A statistical function 13 is used for providing a value proportional to the magnitude of the heartbeat rate variation or to that of the total or partial power of a spectrum derived from the instantaneous heartbeat rate. The instantaneous heartbeat rate variation is compared in block 15 with the corresponding heartbeat rate variation values of the previously determined exertion levels, and the stress caused by the training in relation to the exertion levels, calculated on the basis of the instantaneous heartbeat rate variation, is indicated on the heartbeat rate monitor.

Preferably, the heartbeat rate variation values of a person, corresponding to exertion levels determined during one or more training periods, are stored in the memory of the heartbeat rate monitor he uses, and are used as reference values for heartbeat rate variation values measured during a corresponding training period performed in each particular case to control the stress caused by the training. It is thus possible to store the heartbeat rate variation target values of different sports or fitness forms or those of training periods of different lengths. The heartbeat rate variation and the exertion level can easily be presented by means of heartbeat rate values to the user of the heartbeat rate monitor by comparing measured heartbeat rate values with heartbeat rate values obtained from a heartbeat rate variation value conversion table drawn up for the person concerned. The heartbeat rate values converted from the heartbeat rate variation values can be presented for instance as percentages of the maximum heartbeat rate of the person.

The heartbeat rate monitor of the invention preferably comprises a display element (cf. FIG. 3), which displays, on a real-time basis, an index number and/or a graphic indicator proportional to the heartbeat rate variation, for instance a bar, the height of which is in some manner proportional to the calculated heartbeat rate variation. Naturally, it is also possible to display other information useful during the training on the display of the heartbeat rate monitor, such as time, timing, and/or the measurement result of some other physiological quantity.

Figure 7A:
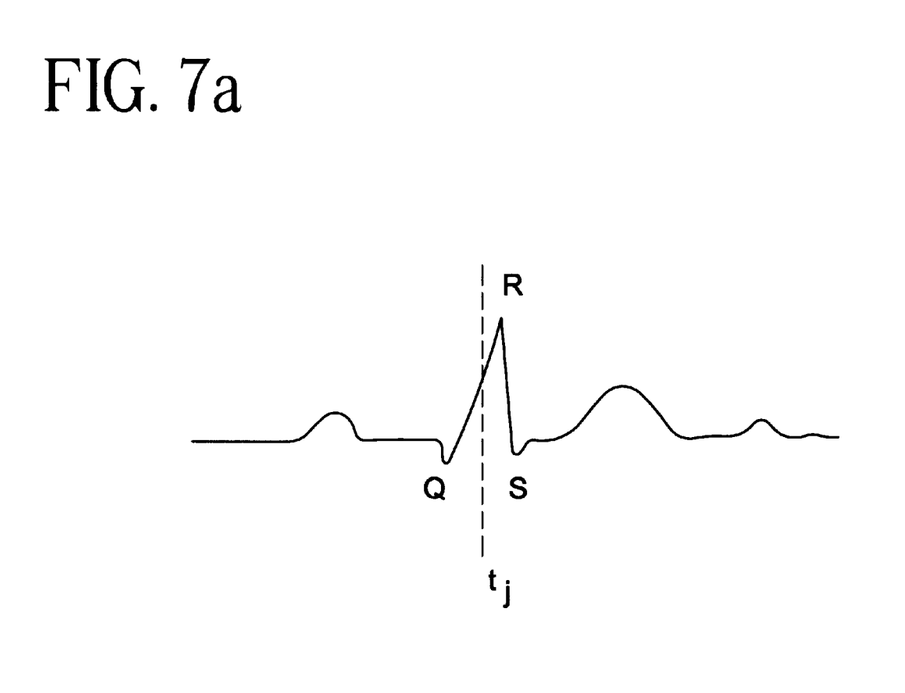
FIGS. 7a–7e show the forming of a heartbeat rate variation signal from an ECG signal.
Figure 7B:
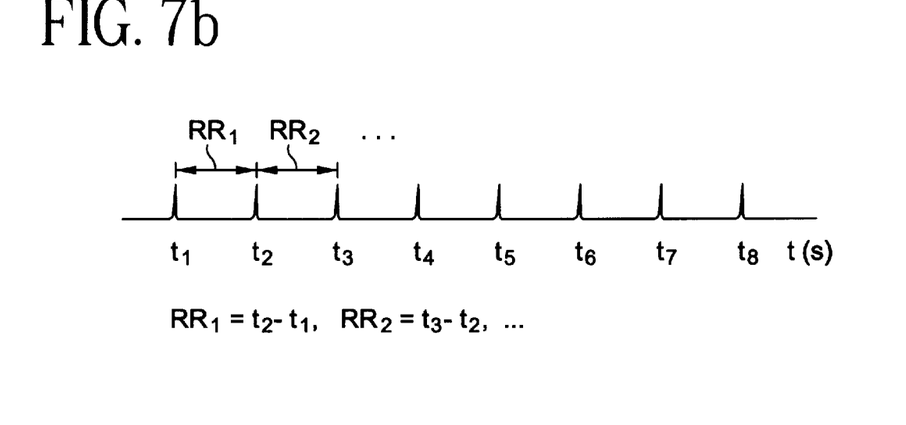
Figure 7C:
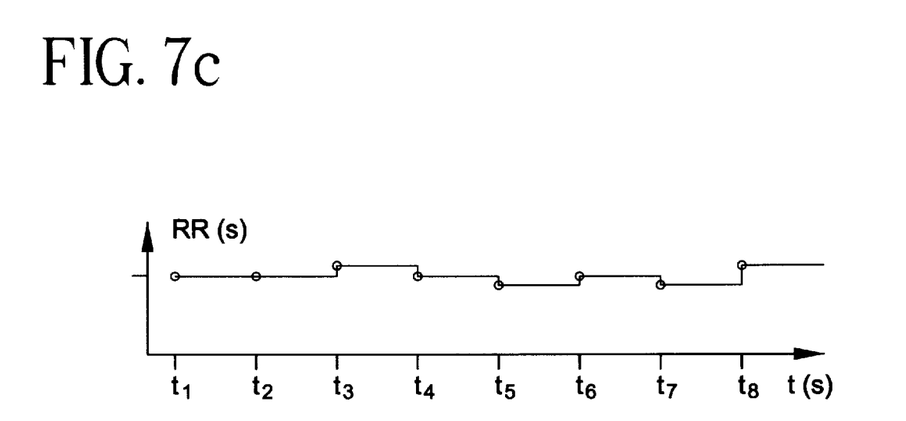
Figure 7D:
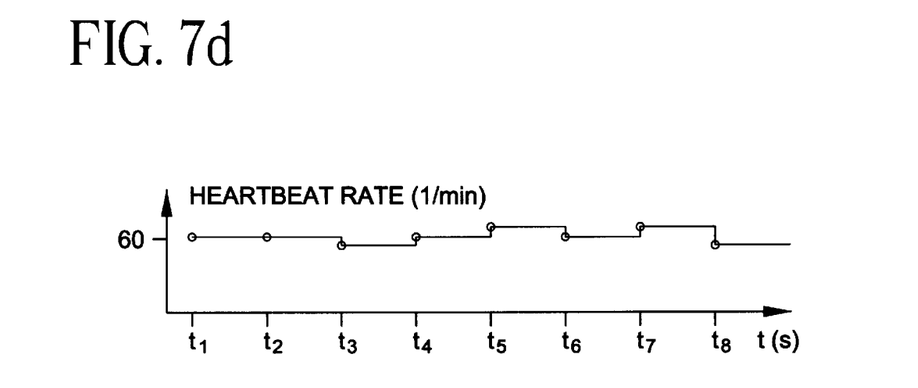
Figure 7E:
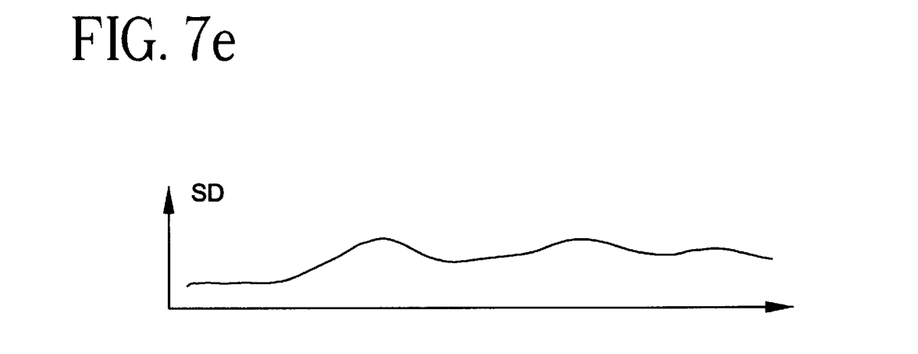

FIGS. 7a–7e show examples of how a heartbeat rate variation signal is derived from an ECG signal. The starting point is the measured ECG signal according to FIG. 1, in which a suitable timing point $t_i$ (FIG. 7a) is determined on the basis of R pulses. FIG. 7b shows the determination of instantaneous heartbeat rate on the basis of the timing points $t_1 \ldots t_n$ of R—R intervals. The instantaneous heartbeat rate is shown as a continuous signal in an R—R time domain in FIG. 7c and in a heartbeat rate time domain in FIG. 7d, the heartbeat rate equalling 60/RR in the heartbeat rate time domain. FIG. 7e shows a heartbeat rate variation graph, which can be calculated directly from the R—R intervals (FIG. 7b) as a recursively moving standard deviation, or as a moving height or width determined from the shape of the distribution pattern, or as a value of the partial or total power of a spectrum derived from the signals of FIG. 7c or 7d.

It will be apparent to one skilled in the art that the different embodiments of the invention are not restricted to the examples presented above but they can freely vary within the scope of the claims presented below.

What is claimed is:

1. A method for determining exertion levels of a person engaged in at least one of fitness and athletic training by means of heartbeat rate measurement during a predetermined training period, wherein the person is subjected to increasing exertion during the training period, said method comprising the steps of:

(a) measuring, by means of a heartbeat rate monitor, an ECG signal of the person and a timing moment of at least one waveform of the ECG signal during the training period;

(b) calculating heartbeat rate via corresponding ECG signal waveform distances to provide a heartbeat rate signal;

(c) subsequent to step (b) and prior to step (d), removing slow processes from said heartbeat rate signal;

(d) providing a proportional value which is proportional to at least one of:

magnitude of the heartbeat rate variation;

total power of a spectrum derived from the heartbeat rate; and partial power of a spectrum derived from the heartbeat rate by means of a mathematical function; and (e) registering the proportional values during the training period as a time function and determining at least those exertion levels of the person which are essential as regards to the training period concerned on the basis of the proportional values.

2. A method for determining exertion levels of a person engaged in at least one of fitness and athletic training and for determining stress caused by the training by means of heartbeat rate measurement during a training period, wherein the person is subjected to increasing exertion at least at the beginning of the training period, said method comprising the steps of:

(a) measuring, by means of a heartbeat rate monitor, an ECG signal of the person and a timing moment of at least one waveform of the ECG signal during the training period;

(b) calculating heartbeat rate via corresponding ECG signal waveform distances;

(c) providing a proportional value which is proportional to at least one of:

magnitude of the heartbeat rate variation;

total power of a spectrum derived from the heartbeat rate; and partial power of a spectrum derived from the heartbeat rate by means of a mathematical function;

(d) registering, at least at the beginning of the training period, within a predetermined time period, the proportional values as a time function and determining at least those exertion levels of the person which are essential as regards the training period concerned on the basis of the heartbeat rate variation values provided within said time period;

(e) comparing, as the training continues past said time period, instantaneous heartbeat rate variation of the person with corresponding heartbeat rate variation values of the determined exertion levels; and (f) indicating on the heartbeat rate monitor the stress caused by the training in relation to the exertion levels, calculated on the basis of the instantaneous heartbeat rate variation.

3. A method for controlling stress caused by training performed by a person engaged in at least one of fitness and athletic training by means of heartbeat rate measurement, said method comprising the steps of:

(a) measuring, by means of a heartbeat rate monitor, and ECG signal of the person and a timing moment of at least one waveform of the ECG signal during the training;

(b) calculating heartbeat rate via corresponding ECG signal waveform distances;

(c) providing a proportional value which is proportional to at least one of:

magnitude of the heartbeat rate variation;

total power of a spectrum derived from the heartbeat rate; and partial power of a spectrum derived from the heartbeat rate by means of a mathematical function;

(e) comparing, during the training, instantaneous heartbeat rate variation of the person with corresponding heartbeat rate variation values of the predetermined exertion levels; and (f) indicating on the heartbeat rate monitor the stress caused by the training in relation to the exertion levels, calculated on the basis of the instantaneous heartbeat rate variation.

4. A method according to claim 1, wherein in step (c), said removing of said slow processes is performed by high pass filtering said heartbeat rate signal.

5. A method according to claim 1, 2 or 3, further comprising the additional steps of:
storing the heartbeat rate variation rate values of a person, corresponding to exertion levels determined during one or more training periods, in a memory of the heartbeat rate monitor which the person uses; and
using said heartbeat rate variation values as reference values for heartbeat rate variation values measured during a corresponding training period performed in each particular case to control stress caused by the training.

6. A method according to any one of the claims 1–3, further comprising the additional step of presenting the exertion level of the person to the user of the heartbeat rate monitor by comparing measured heartbeat rate values with heartbeat rate values obtained from a heartbeat rate variation value conversion table drawn up for the person concerned.

7. A method according to claim 5, wherein the heartbeat rate values converted from the heartbeat rate variation values are presented as percentages of the maximum heartbeat rate of the person.

8. A method according to any one of the claims 2–3, further comprising the additional step of high pass filtering the heartbeat rate signal derived from the ECG signal to remove slow processes distorting the result before the heartbeat rate variation and the exertion levels of the person are determined.

9. A method according to any one of the claims 1–3, wherein the heartbeat rate variation is calculated by means of a statistical function which provides the standard deviation of the heartbeat rate as a result.

10. A method according to any one of the claims 1–3, wherein the heartbeat rate variation is calculated by means of a statistical function which provides at least one of the height and width of the distribution pattern of at least one of an instantaneous heartbeat rate signal and an R—R signal as a result.

11. A method according to any one of the claims 1–3, wherein the quantity proportional to the heartbeat rate variation is calculated by means of a function which provides at least one of the total and partial power of a power spectrum of a continuous heartbeat rate signal as a result.

12. A method according to claim 1, 2 or 3, wherein in step (a), said at least one waveform of the ECG signal is the QRS complex.

13. An apparatus for determining an exertion level of a person engaged in at least one of fitness and athletic training by means of a heartbeat rate monitor, the apparatus comprising:
means for detecting and transmitting heartbeat rate signals;
a heartbeat rate monitor for receiving, calculating and measuring heartbeat rate signals, and for registering a timing moment of at least one ECG signal waveform contained by a heartbeat rate signal;
means for calculating the heartbeat rate on the basis of corresponding ECG signal waveform distances;
means for removing slow processes from said heartbeat rate signal;
means for providing a proportional value which is proportional to at least one of:
magnitude of the heartbeat rate variation;
total power of a spectrum derived from the heartbeat rate; and
partial power of a spectrum derived from the heartbeat rate by means of a mathematical function; and
means for registering the proportional values during the training period as a time function and for determining at least those exertion levels of the person which are essential as regards the training period concerned on the basis of the proportional values.

14. An apparatus for determining exertion levels of a person engaged in at least one of fitness and athletic training and for determining stress caused by the training by means of a heartbeat rate monitor, the apparatus comprising:
means for detecting and transmitting heartbeat rate signals;
a heartbeat rate monitor for receiving, calculating and measuring heartbeat rate signals, and for registering a timing moment of at least one ECG signal waveform contained by a heartbeat rate signal;
means for calculating the heartbeat rate at least at the beginning of the training within a predetermined time period on the basis of corresponding ECG signal waveform distances;
means for providing a proportional value which is proportional to at least one of:
magnitude of the heartbeat rate variation;
total power of a spectrum derived from the heartbeat rate; and
partial power of a spectrum derived from the heartbeat rate by means of a mathematical function; and
means for registering the proportional values as a time function and for determining at least those exertion levels of the person which are essential as regards the training period concerned at least within said predetermined time period on the basis of the heartbeat rate variation values;
means for comparing the instantaneous heartbeat rate variation of the person with the corresponding heartbeat rate variation values of the determined exertion levels; and
means for indicating the stress caused by the training, calculated in relation to the exertion levels, on the heartbeat rate monitor.

15. An apparatus for controlling stress caused by training performed by a person engaged in at least one of fitness and athletic training by means of a heartbeat rate monitor and utilizing predetermined exertion levels, the apparatus comprising:
a heartbeat rate monitor, by means of which heartbeat rate of the person and the timing moment of at least one ECG signal waveform can be measured during the training;
means for calculating the heartbeat rate on the basis of corresponding ECG signal waveform distances;
means for providing a proportional value which is proportional to at least one of:
magnitude of the heartbeat rate variation;
total power of a spectrum derived from the heartbeat rate; and
partial power of a spectrum derived from the heartbeat rate by means of a statistical function;
means for comparing the instantaneous heartbeat rate variation of the person during the training with corresponding heartbeat rate variation values of the predetermined exertion levels; and
means for indicating the stress caused by the training, calculated in relation to the exertion levels, on the heartbeat rate monitor.

16. The apparatus of claim 13, wherein said means for removing slow processes from said heartbeat rate signal is a high pass filter.

17. An apparatus according to claim 13, 14 or 15, wherein the heartbeat rate monitor further comprises:

a computer; and memory means for storing the exertion levels of the person, determined during at least one training period, and for using said exertion levels as reference values for measured heartbeat rate variation values to control the stress caused by a corresponding training period performed in each particular case.

18. An apparatus according to any one of the claims 13–15, further comprising:

a display on said heart rate monitor; and means for comparing heartbeat rate values measured during the training with heartbeat rate values obtained from a heartbeat rate variation value conversion table drawn up in advance, in order to indicate the exertion level on the display of the heartbeat rate monitor by means of a scale including heartbeat rate values.

19. An apparatus according to claim 15, wherein the scale including heartbeat rate values is a percentage scale of the measured heartbeat rate of the maximum heartbeat rate of a person.

20. An apparatus according to any one of the claims 14, 15, further comprising a high pass filter for filtering a heartbeat rate signal.

21. An apparatus according to any one of claims 13–15, wherein said at least one ECG signal waveform is the QRS complex.

* * * * *

UNITED STATES PATENT AND TRADEMARK OFFICE
CERTIFICATE OF CORRECTION

PATENT NO. : 6,104,947
DATED : August 15, 2000
INVENTOR(S) : Heikkila et al.

It is certified that error appears in the above-identified patent and that said Letters Patent is hereby corrected as shown below:

Column 8,
Line 38, now reads "heartbeat rare" should read -- heartbeat rate --;

Column 10,
Line 57, now reads "(e)" should read -- (d) --;
Line 61, now reads "(f)" should read -- (e) --.

Signed and Sealed this

Eighteenth Day of December, 2001

Attest:

JAMES E. ROGAN
*Attesting Officer*   *Director of the United States Patent and Trademark Office*